(12) United States Patent
Birrenbach

(10) Patent No.: US 6,803,063 B2
(45) Date of Patent: Oct. 12, 2004

(54) PHOTOSTABILIZATION OF DIBENZOYLMETHANE DERIVATIVES

(75) Inventor: Gerd Birrenbach, Kappel (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 145 days.

(21) Appl. No.: 10/275,870

(22) PCT Filed: May 3, 2001

(86) PCT No.: PCT/CH01/00275
§ 371 (c)(1), (2), (4) Date: Nov. 8, 2002

(87) PCT Pub. No.: WO01/85123
PCT Pub. Date: Nov. 15, 2001

(65) Prior Publication Data
US 2003/0185770 A1 Oct. 2, 2003

(30) Foreign Application Priority Data
May 12, 2000 (CH) .................................. 93300

(51) Int. Cl.[7] ............. A61K 7/42; A61K 7/44; A61K 7/00; A61K 31/53

(52) U.S. Cl. ............. 426/59; 424/60; 424/400; 424/401; 514/241

(58) Field of Search ............. 424/59, 60, 400, 424/401; 514/241

(56) References Cited

U.S. PATENT DOCUMENTS 6,328,981 B1   12/2001   Boussouira et al.   ........ 424/401

FOREIGN PATENT DOCUMENTS

| DE | 19756921 | 6/1999 |
| DE | 19846772 | 4/2000 |
| EP | 0845261 | 6/1998 |
| EP | 0880962 | 12/1998 |

*Primary Examiner*—Shelley A. Dodson
(74) *Attorney, Agent, or Firm*—Kevin T. Mansfield

(57) ABSTRACT

By using 2,4-bis[[4-(2-ethylhexyloxy)-2-hydroxy]phenyl]-6-(4-methoxyphenyl)-1,3,5-triazine, the photostability of dibenzoylmethane derivatives is substantially improved and, indirectly, stabilisation of cinnamic acid esters is also effected, by which means there are made possible photostable cosmetic compositions for protection against UV radiation which have a high sun protection factor and a high absorbance in both the UVA and UVB range.

19 Claims, No Drawings

PHOTOSTABILIZATION OF DIBENZOYLMETHANE DERIVATIVES

The invention relates to the use of 2,4-bis[[4-(2-ethylhexyloxy)-2-hydroxy]phenyl]-6-(4-methoxyphenyl)-1,3,5-triazine for improving the photstability of dibenzoylmethane for improving the photostability of dibenzoylmethane derivatives and to corresponding cosmetic compositions for protecting against UV radiation and to the production of such compositions.

There is a growing need for good topical sun protection preparations in order to prevent the damaging effects of UV light on human skin, for example sunburn, photo-allergic reactions, premature ageing of the skin and skin cancer. Most sun protection preparations now provide good protection against ultraviolet radiation in the wavelength range from 290 to 320 nm (UV-B range). Because numerous studies in recent years have shown that ultraviolet radiation in the wavelength range from 320 to 400 nm (UV-A range) makes a significant contribution to the skin damage caused by sunlight, there is also an increasing requirement for adequate protection against UVA radiation. In addition, the availability of sun protection preparations having a high sun protection factor (hereinafter also referred to as SPF) has led to concerns that users are able to stay in the sun for longer and, as a result, are exposed to an increased amount of UVA radiation.

A UV filter should, ideally, convert absorbed UV radiation quickly and efficiently into harmless thermal energy without, in the process, the UV filter and its protective action being degraded or the function and reliability of the sun protection preparation being impaired. Although there is a large selection of suitable UVB filters, good UVA absorbers are rare because they are mostly of low activity or of inadequate photostability. In particular, dibenzoylmethane derivatives, for example 4-tert-butyl-4'-methoxydibenzoylmethane, the most common UVA filter, which is obtainable commercially, for example, under the designation Parsol 1789 (Givaudan, Switzerland), are degraded relatively quickly under the action of sunlight and, as a result, lose their protective action (R. M. Sayre et al., Allured's Cosmetics & Toiletries, 114 (5): 85–91, 1999). In addition, it is known that the otherwise photostable cinnamic acid esters, which are active as UVB filters, such as 4-methoxycinnamic acid 2-ethylhexyl ester (usually designated octyl methoxycinnamate), which is frequently used in combination with dibenzoylmethanes and which is available, for example, under the tradename Parsol MCX (LaRoche, Switzerland), may, after photoreaction of the dibenzoylmethane derivative, form cycloaddition products with the latter and consequently become destabilised.

For improving the photostability of dibenzoylmethane derivatives, EP-A-0 815 834 has proposed certain amides such as, especially, N,N-diethyl-methylbenzamide and N-butyl-N-acetyl-3-aminopropionic acid ethyl ester. For the same purpose, EP-A-0 970 961 discloses the addition of certain silicon compounds having a benzylidene camphor function. Furthermore, a first photostable UVA filter has been disclosed, namely the terephthalylidene dicamphor sulfonic acid obtainable under the designation Mexoryl SX (Chimex, France), which is water-soluble and has a strong absorption maximum at 345 nm.

DE-A-197 56 921 has also proposed the use of synthetic beeswax for increasing the UV-A-protective performance of cosmetic or dermatological formulations comprising at least one conventional UV-A filter substance and/or a broad-spectrum filter substance, there also being mentioned without any data, inter alia, an O/W lotion comprising 2,4-bis-[[4-(2-ethylhexyloxy)-2-hydroxy]phenyl]-6-(4-methoxyphenyl)-1,3,5-triazine and 4-tert-butyl-4'-methoxydibenzoylmethane in addition to 12 further components.

It has now been found, surprisingly, that the broad-spectrum filter 2,4-bis-[[4-(2-ethylhexyloxy)-2-hydroxy]phenyl]-6-(4-methoxyphenyl)-1,3,5-triazine, which has recently come on the market under the designation Tinosorb S (Ciba Speciality Chemicals, Switzerland), is suitable for substantially improving the photostability of dibenzoylmethane derivatives such as 4-tert-butyl-4'-methoxydibenzoylmethane, and that, by that means, destabilisation of cinnamic acid esters such as 4-methoxycinnamic acid 2-ethylhexyl ester can very largely be avoided. In addition, 2,4-bis[[4-(2-ethylhexyloxy)-2-hydroxy]phenyl]-6-(4-methoxyphenyl)-1,3,5-triazine supplements the spectral range of the dibenzoylmethanes and as a result additionally contributes to the protective action of products comprising such compounds.

The invention accordingly relates to the use of 2,4-bis[[4-(2-ethylhexyloxy)-2-hydroxy]-phenyl]-6-(4-methoxyphenyl)-1,3,5-triazine for improving the photostability of dibenzoylmethane derivatives. The invention relates especially to the use of 2,4-bis[[4-(2-ethylhexyloxy) 2-hydroxy]phenyl]-6-(4-methoxyphenyl)-1,3,5-triazine in or for the production of a cosmetic composition comprising a dibenzoylmethane derivative, for the purpose of improving the photostability of the dibenzoylmethane derivative. The stabilisation can in principle be achieved by bringing an effective amount of 2,4-bis[[4-(2-ethylhexyloxy)-2-hydroxy]phenyl]-6-(4-methoxyphenyl)-1,3,5-triazine into contact with the dibenzoylmethane derivative or by incorporating them into the composition.

The invention relates also to cosmetic compositions (especially so-called sun protection preparations or light protection preparations) for topical use for protection against UV radiation, especially sunlight, comprising a cosmetically acceptable carrier, at least one dibenzoylmethane derivative, at least one cinnamic acid ester and an effective amount of 2,4-bis[[4-(2-ethylhexyloxy)-2-hydroxy]phenyl]-6-(4-methoxyphenyl)-1,3,5-triazine. In accordance with the invention, such compositions may be produced by incorporating the dibenzoylmethane derivative, the cinnamic acid ester and 2,4-bis[[4-(2-ethylhexyloxy)-2-hydroxy]phenyl]-6-(4-methoxyphenyl)-1,3,5-triazine into the cosmetically acceptable carrier.

2,4-Bis[[4-(2-ethylhexyloxy)-2-hydroxy]phenyl]-6-(4-methoxyphenyl)-1,3,5-triazine, which according to INCI nomenclature is designated Bis Ethylhexyloxyphenol Methoxyphenyl Triazine or, in the context of the present invention, is also abbreviated to EHPT, is, as mentioned, a known broad-spectrum filter, which is commercially available under the name Tinosorb S (Ciba Speciality Chemicals, Switzerland). The cosmetic compositions obtainable in accordance with the invention may contain typically about from 0.1 to 15% by weight, preferably about from 0.5 to 10% by weight, 2,4-bis[[4-(2-ethylhexyloxy)-2-hydroxy]phenyl]-6-(4-methoxyphenyl)-1,3,5-triazine.

In accordance with the invention, any dibenzoylmethane derivative that is active as a UV filter is, in principle, suitable as the dibenzoylmethane derivative, especially alkyl- and/or alkoxy-substituted dibenzoylmethanes, such as 2-methyldibenzoylmethane, 4-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4'-diisopropyldibenzoylmethane, 4,4'-dimethoxydibenzoylmethane, 4-tert-butyl-4'- methoxydibenzoylmethane, 2-methyl-5-isopropyl-4'-methoxydibenzoylmethane, 2-methyl-5-tert-butyl-4'-methoxydibenzoylmethane, 2,4-dimethyl-4'-methoxydibenzoylmethane and 2,6-dimethyl-4-tert-butyl-4'-methoxydibenzoylmethane. Dibenzoylmethane derivatives that are preferably used are 4-isopropyldibenzoylmethane, which is available under the name Eusolex 8020 (Merck, Germany) and, especially, 4-tert-butyl-4'-methoxydibenzoylmethane, which is available, for example, under the name Parsol 1789 (Givaudan, Switzerland). Typically, the cosmetic compositions obtainable in accordance with the invention may contain about from 0.1 to 10% by weight dibenzoylmethane derivative, with preference generally being given to amounts of about from 0.5 to 5% by weight.

Because the dibenzoylmethane derivatives such as 4-tert-butyl-4'-methoxydibenzoylmethane are UVA filters having low absorbance in the UVB range, the use of dibenzoylmethane derivatives alone results in merely low sun protection factors (which, in addition, rapidly diminish under the action of sunlight) and comparatively high values of the ratio of UVA absorbance to UVB absorbance (in the context of the present invention, the ratio is also referred to as the UVA/UVB ratio; cf. R. Stokes in: B. Gabard et al., Dermatopharmacology of Topical Preparations, Springer-Verlag Berlin, 2000, pages 365–382). Although, by using cinnamic acid esters that are active as UVB filters, such as 4-methoxycinnamic acid 2-ethylhexyl ester and 4-methoxycinnamic acid isoamyl ester, in combination with dibenzoylmethane derivatives, it is possible to achieve sun protection factors that are very high initially and UVA/UVB ratios of about, or less than, 1, the protective action is rapidly lost as a result of the photoinstability of the dibenzoylmethane derivatives and the destabilisation of the cinnamic acid esters caused by that photoinstability.

In contrast, by using dibenzoylmethane derivatives in combination with 2,4-bis-[[4-(2-ethylhexyloxy)-2-hydroxy]phenyl]-6-(4-methoxyphenyl)-1,3,5-triazine, it is possible to achieve long-lasting high sun protection factors and stable UVA/UVB ratios of, for example, about from 0.6 to 1.5, especially about 0.8 to 1.1, that is to say uniform and lasting protection in both the UV-A and UV-B range.

In addition, destabilisation of cinnamic acid esters in the presence of dibenzoylmethane derivatives is substantially avoided by means of 2,4-bis[[4-(2-ethylhexyloxy)-2-hydroxy]-phenyl]-6-(4-methoxyphenyl)-1,3,5-triazine as a result of which the invention also makes possible photostable cosmetic compositions that comprise a cinnamic acid ester (active as a UVB filter) in combination with a dibenzoylmethane derivative. In accordance with a preferred aspect of the present invention, therefore, 2,4-bis[[4-(2-ethylhexyloxy)-2-hydroxy]phenyl]-6-(4-methoxyohenyl)-1,3,5-triazine can be used in or for the production of a cosmetic composition comprising a dibenzoylmethane derivative and a cinnamic acid ester and the cosmetic composition can comprise a cosmetically acceptable carrier, at least one dibenzoylmethane derivative, at least one cinnamic acid ester, such as 4-methoxycinnamic acid 2-ethylhexyl ester or 4-methoxycinnamic acid isoamyl ester, and an effective amount of 2,4-bis[[4-(2-ethylhexyloxy)-2-hydroxy]phenyl]-6-(4-methoxyphenyl)-1,3,5-triazine. The content of cinnamic acid ester in the cosmetic compositions obtainable in accordance with the invention may be typically about from 0.1 to 15% by weight, preferably about from 0.5 to 10% by weight.

The combination according to the invention of 2,4-bis[[4-(2-ethylhexyloxy)-2-hydroxy]phenyl]-6-(4-methoxyphenyl)-1,3,5-triazine with dibenzoylmethane derivatives is suitable in principle for use in any customary forms of use, especially liquid or semi-solid forms which are suitable for application to the skin and/or hair, such as aqueous, oily or alcoholic solutions, hydrophilic (aqueous) or lipophilic (oily) gels, emulsions of the O/W (oil-in-water emulsion), W/O (water-in-oil emulsion), W/O/W or O/W/O type, and also creams or lotions, colloidal systems such as microemulsions, nanoemulsions, mixed micellar solutions, liposomal systems, nanosuspensions etc. and hydrophilic or lipophilic suspensions. Production may be carried out in a manner known per se using conventional cosmetic carrier materials, it being possible to obtain cosmetic products in the form of a cream, lotion, milk or paste, balsam, spray, gel, stick etc., depending on composition and consistency; appropriate pointers are to be found, for example, in Cosmetics & Toiletries 105 : 91–94, 1990 and 113 : 83–98, 1998, and also in textbooks and standard works on cosmetics.

The cosmetic compositions obtainable in accordance with the invention may be preferably emulsions, especially O/W emulsions or W/O emulsions. Special preference is given to phospholipid-containing emulsions, especially phospholipid-containing O/W emulsions, because it has been found that, by that means, the photostability can be further improved and also an improvement in skin penetration and water-resistance can be achieved.

Besides comprising the UV filters, preferred oil-in-water emulsions comprise typically (a) an aqueous phase comprising water and conventional excipients such as thickeners or viscosity-increasing agents (e.g. carbomer), humectants or hydrating agents (e.g. sorbitol and/or glycerol), buffer substances in the pH range of about from 4 to 8, preferably of about from 5.5 to 7.0, or agents for adjusting the pH to such a value (e.g. trometamine or triethanolamine) and preservatives (e.g. parabens such as methylparaben and/or propylparaben); (b) emulsifier(s), typically a mixture of surface-active agents, such as polysorbate 20, sorbitan laurate, cetearyl alcohol and/or acrylate/($C_{10-30}$alkyl) acrylate cross-polymers; and (c) a lipophilic phase comprising vegetable, animal or synthetic oils (e.g. silicones) and or lipophilic solvents, such as dicaprylyl maleate, dimethicone, ($C_{12-15}$alkyl) benzoate and/or triglycerides of $C_{8-18}$ fatty acids, ethylhexyl palmitate and paraffin.

Besides comprising the UV filters, preferred water-in-oil emulsions comprise typically (a) an aqueous phase comprising water and conventional excipients such as sodium lactate and lactic acid and also preservatives (e.g. parabens such as methylparaben and/or propylparaben); (b) emulsifier(s) such as PEG-7-hydrogentated castor oil (polyethylene glycol derivative of hydrogenated castor oil containing on average 2 mol of ethylene oxide), methoxy-PEG-22/dodecylglycol copolymer and/or ethoxylated glycerol sorbitan esters of saturated fatty acids; and (c) a lipophilic phase comprising vegetable, animal or synthetic oils (e.g. silicones) and/or lipophilic solvents, such as myristyl lactate, triglycerides of $C_{8-18}$ fatty acids, paraffin and/or dimethicone.

Phospholipid-containing emulsions can have a similar composition to the O/W or W/O emulsions described, with, however, at least one emulsifier being a phospholipid, preferably lecithin. The addition of phospholipid modifies the properties of the lipophilic phase, as a result of which liposomal structures can be formed and skin penetration and water-resistance are improved. Besides comprising the UV filters, preferred phospholipid-containing oil-in-water emulsions comprise typically (a) an aqueous phase comprising water and conventional excipients such as thickeners or viscosity-increasing agents (e.g. carbomer), humectants or hydrating agents (e.g. sorbitol and/or glycerol), buffer substances in the pH range of about from 4 to 8, preferably of about from 5.5 to 7.0, or agents for adjusting the pH to such a value (e.g. tromethamine) and preservatives (e.g. parabens such as methylparaben and/or propylparaben); (b) emulsifier (s), especially at least one phospholipid such as lecithin, optionally in combination with further emulsifiers such as stearic acid and/or triceteareth-4 phosphate; and (c) a lipophilic phase comprising vegetable, animal or synthetic oils (e.g. silicones) and or lipophilic solvents, such as dicaprylyl maleate, dimethicone, ($C_{12-15}$alkyl) benzoate and/or triglycerides of $C_{8-18}$ fatty acids, ethylhexyl palmitate and paraffin. For example, such a formulation may comprise water, ethanol, carbomer, triethanolamine or tromethamine 20, aloe vera gel, sorbitol, cetyl phosphate, cetyl alcohol, dicaprylyl maleate, lecithin, dimethicone, tocopherol acetate, methylparaben, propylparaben, 2,4-bis[[4-(2-ethylhexyloxy)-2-hydroxy]phenyl]-6-(4-methoxyphenyl)-1, 3,5-triazane, 4-tert-butyl-4'-methoxydibenzoylmethane, 4-methoxycinnamic acid 2-ethylhexyl ester and, if desired, further UV filters.

That formulation and further phospholipid-containing liposomal formulations may be produced in a manner known per se, for example by the methods described in WO-A-89/11850 and U.S. Pat. No. 5,269,979. However, it has been found that, generally, suitable formulations can also be obtained more simply by preparing the emulsion by mixing a solution of the phospholipid in an alcohol, preferably ethanol, into the lipophilic phase and then producing an emulsion in a manner known per se by means of homogenisation with the aqueous phase using suitable apparatus.

The cosmetic compositions obtainable in accordance with the invention may also comprise further UV filters, for example benzophenones such as 2-hydroxy-4-methoxybenzophenone (oxybenzone) or 2-hydroxy-4-methoxybenzophenone 5-sulfonic acid (sulisobenzone); p-aminobenzoic acid or derivatives such as 4-bis(2-hydroxypropyl)aminobenzoic acid ethyl ester, octyldimethyl p-aminobenzoate, 4-dimethylaminobenzoic acid 2-ethylhexyl ester, ethoxylated ethyl 4-aminobenzoate or 4-bis(polyethoxy)aminobenzoic acid polyoxyethyl ester, camphor derivatives such as 3-(4'-methylbenzylidene) camphor, 3-benzylidene camphor, benzylidene camphor sulfonic acid or terephthalylidene dicamphor sulfonic acid, benzimidazole derivatives such as 2-phenylbenzimidazole 5-sulfonic acid, which is water-soluble; salicylates such as 3,3,5-trimethylcyclohexyl salicylate (homosalatum), salicylic acid 2-ethylhexyl ester (octyl salicylate) or 4-isopropylbenzyl salicylate or 2,4,6-trianilino-(p-carbo-2'-ethylhexyl-1-'-oxy)-1,3,5-triazine; 3-(4'-trimethylammonium)-benzylidene-bornan-2-one methyl sulfate or 2-cyano-3,3-diphenylacrylic acid (2-ethylhexyl ester) (octocrylene).

In addition to the UV filters, the cosmetic compositions obtainable in accordance with the invention may, if desired, also comprise micropigments or nanopigments (pigments in micronised form) as so-called sun-blockers. Suitable materials, particle sizes and methods are described, for example, in EP-A-0 433 086 and by M. W. Anderson et al. in N. J. Lowe et al., Sunscreens: Development, Evaluation, and Regulatory Aspects, Marcel Dekker Inc., New York, 1997, pages 353–397. As micropigments there may preferably be used titanium dioxide having a particle size of <35 µm, especially <10 µm, and/or zinc oxide having a particle size of <50 µm, especially <20 µm.

The cosmetic compositions obtainable in accordance with the invention may also comprise further excipients that are customary in cosmetic products, such as, for example, anti-oxidants, perfume oil, skin-care agents, vitamins, film-formers and/or water-resistance-improvers, e.g. biotin, dexpanthenol, aloe vera gel, tocopherol acetate, acrylate/ ($C_{10-30}$alkyl) acrylate cross-polymers, PVP-icosene copolymers and the like.

The present invention is further illustrated by the Examples that follow, wherein the designations and abbreviations used for components have the following meanings:

carbomer is an acrylic acid homopolymer cross-linked with an allyl ether of pentaerythritol, with an allyl ether of sucrose or with an allyl ether of propylene, and is commercially available, for example, under the designation Carbopol 940 (BF Goodrich, USA); tromethamine 20% denotes an aqueous solution containing 20% by weight 2-amino-2-(hydroxymethyl)-1,3-propanediol;

sorbitol 70% denotes an aqueous solution containing 70% by weight sorbitol; sodium lactate solution is an aqueous solution containing 50% by weight sodium lactate;

polysorbate 20 is a mixture of lauric acid esters of sorbitol and sorbitol anhydrides, which consists mainly of the monoester condensed with about 20 mol of ethylene oxide and is also known as polydxyethylene(20) sorbitan monolaurate;

sorbitan laurate is commercially available, for example, as Tween 20 (Uniqema Americas, USA);

ceteary1 alcohol denotes a mixture of fatty alcohols, which consists mainly of cetyl alcohol and stearyl alcohol and is available, for example, under the name Hyfatol CS (Aarhus, Denmark);

triceteareth-4 phosphate is a mixture of mono-di-tri(alkyl tetraglycol ether)-O-phosphoric acid esters wherein the alkyl radicals have mainly from 16 to 18 carbon atoms and which is commercially available under the designation Hostaphat KW 340 N (Clariant GmbH, Germany);

PEG-7-hydr. castor oil denotes a polyethylene glycol derivative of hydrogenated castor oil containing on average 7 mol of ethylene oxide per mol of castor oil, and is available, for example, as Arlacel 989 (Uniqema Americas, USA);

methoxy-PEG-22/dodecyl glycol copolymer is a polymer of formula $CH_3O(CH_2CH_2)_x[CH_2CH(C_{10}H_{21})O]_yH$ wherein x has an average value of 22 and y has an average value of 7, which is commercially available, for example, under the designation Elfacos E 200 (Akzo Nobel, Netherlands);

Arlacel 582 (ICI, Great Britain) is an ethoxylated glycerol sorbitan ester of saturated fatty acids;

dicaprylyl maleate denotes the diester of capryl alcohol and maleic acid;

lecithin is commercially available, for example, under the designation Phospholipon (Nattermann, Germany);

dimethicone is a mixture of completely methylated linear polysiloxane polymers having terminal trimethylsiloxy groups, which is commercially available, for example, under the name AEC Dimethicone (350 CS) (A & E Connock, Great Britain);

($C_{12}$–$C_{15}$alkyl) benzoate denotes a mixture of alkyl benzoates containing from 12 to 15 carbon atoms in the alkyl radical, and is commercially available, for example, under the name Finsolv TN (Finetex, USA);

as medium-chain-length triglyceride there was used a mixture consisting mainly of triglycerides of $C_{8-12}$ fatty acids such as Miglyol 812 neutral oil (Condea Chemie, Germany);

paraffin (mineral oil) denotes a mixture of hydrocarbons in accordance with the term "Paraffinum Liquidum" according to the European Pharmacopoeia;

methylparaben denotes p-hydroxybenzoic acid methyl ester;
propylparaben denotes p-hydroxybenzoic acid propyl ester;
AVB or avobenzone is the UVA filter 4-tert-butyl-4'-methoxydibenzoylmethane and is available, for example, under the designation Parsol 1789 (LaRoche, Switzerland);
OMC or octyl methoxycinnamate is the UVB filter 4-methoxycinnamic acid 2-ethylhexyl ester and is available, for example, under the designation Parsol MCX (LaRoche, Switzerland);
EHPT or Bis Ethylhexyloxyphenol Methoxyphenyl Triazine is the broad-spectrum filter 2,4-bis[[4-(2-ethylhexyloxy)-2-hydroxy]phenyl]-6-(4-methoxyphenyl)-1,3,5-triazine and is commercially available under the designation Tinosorb S (Ciba Speciality Chemicals, Switzerland).

The in vitro determination of the sun protection factor was carried out according to the method of Diffey and Robson (B. L. Diffey and J. Robson, J. Soc. Cosmet. Chem. 40: 127–133,1989 ; B. L. Diffey et al., Eur. J. Dermatol. 7: 226–228, 1997) by means of an SPF-measuring system having a 150 W xenon lamp and 35×35 mm quartz plates from Glen Spectra (Great Britain) and using Transpore tapes (Minnesota Mining & Manufacturing, USA). In each case, the sun protection product being investigated was applied in an amount of 2 mg/cm$^2$ to two quartz plates. One plate was irradiated with UV light from the xenon lamp, which was optically filtered to simulate summer sunlight (Multiport Solar UV Simulator Model 501, Solar Light, Philadelphia, USA). The other plate was left unirradiated as a control (stored in an incubating cabinet at 30° C). The UV radiation intensity was set at 5.5 mW/cm$^2$.

After irradiation with 30 MED (1 MED=25 mJ/cm$^2$= minimum erythemal dose), the spectral transmission of the irradiated sample and of the non-irradiated control sample was measured.

In addition, the ratio of the UVA absorbance to the UVB absorbance (in the context of the present invention also referred to as the UVA/UVB ratio) was determined by the method described by R. Stokes (in: B. Gabard et al., Dermatopharmacology of Topical Preparations, Springer-Verlag Berlin, 2000, pages 365–382), and the sun protection products were also tested by means of high-pressure liquid chromatography after being dissolved away from the quartz plate.

EXAMPLE 1

O/W Emulsions

In order to produce the O/W emulsions listed in Table 1, carbomer was in each case dispersed in water; sorbitol 70% and methylparaben were added to the dispersion, and the resulting aqueous phase was heated to 80° C. Polysorbate 20, sorbitan laurate, cetearyl alcohol, dicaprylyl maleate, dimethicone, ($C_{12-15}$alkyl) benzoate, propylparaben and the UV filters AVB, OMC and/or EHPT were mixed in a separate vessel, heated to 80° C. and then added to the heated aqueous phase. The mixture was homogenised for about 2 minutes, then cooled to ambient temperature, adjusted to a pH of 6.0–6.5 by adding tromethamine 20%, and again homogenised for about 2 minutes.

In accordance with the in vitro methods described above, the effect of UV light (30 minutes' irradiation with 30 MED) on the protective properties and the stability of the O/W emulsions was investigated. The measured sun protection factors and UVA/UVB ratios and their percentage changes (relative to the initial value), and the percentage degradation of AVB and/or OMC determined by means of HPLC, are indicated in Table 2. The values indicated are, in each case, averages (including scatter) from 3 measurements.

TABLE 1

O/W formulations: compositions in % by weight

| Components | 1A | 1B | 1C | 1D | 1E | 1F | 1G | 1H | 1I | 1J | 1K | 1L | 1M |
| --- | --- | --- | --- | --- | --- | --- | --- | --- | --- | --- | --- | --- | --- |
| water | 74.7% | 72.2% | 67.2% | 72.1% | 67.1% | 62.2% | 69.7% | 62.2% | 57.2% | 79.6% | 77.2% | 74.7% | 67.2% |
| carbomer | 0.2% | 0.2% | 0.2% | 0.2% | 0.2% | 0.2% | 0.2% | 0.2% | 0.2% | 0.2% | 0.2% | 0.2% | 0.2% |
| tromethamine 20% | 0.7% | 0.7% | 0.7% | 0.8% | 0.8% | 0.7% | 0.7% | 0.7% | 0.7% | 0.8% | 0.7% | 0.7% | 0.7% |
| sorbitol 70% | 3.0% | 3.0% | 3.0% | 3.0% | 3.0% | 3.0% | 3.0% | 3.0% | 3.0% | 3.0% | 3.0% | 3.0% | 3.0% |
| polysorbate 20 | 3.0% | 3.0% | 3.0% | 3.0% | 3.0% | 3.0% | 3.0% | 3.0% | 3.0% | 3.0% | 3.0% | 3.0% | 3.0% |
| sorbitan laurate | 3.0% | 3.0% | 3.0% | 3.0% | 3.0% | 3.0% | 3.0% | 3.0% | 3.0% | 3.0% | 3.0% | 3.0% | 3.0% |
| cetearyl alcohol | 1.0% | 1.0% | 1.0% | 1.0% | 1.0% | 1.0% | 1.0% | 1.0% | 1.0% | 1.0% | 1.0% | 1.0% | 1.0% |
| dicaprylyl maleate | 3.0% | 3.0% | 3.0% | 3.0% | 3.0% | 3.0% | 3.0% | 3.0% | 3.0% | 3.0% | 3.0% | 3.0% | 3.0% |
| dimethicone | 0.5% | 0.5% | 0.5% | 0.5% | 0.5% | 0.5% | 0.5% | 0.5% | 0.5% | 0.5% | 0.5% | 0.5% | 0.5% |
| ($C_{12}$–$C_{15}$alkyl) benzoate | 3.0% | 3.0% | 3.0% | 3.0% | 3.0% | 3.0% | 3.0% | 3.0% | 3.0% | 3.0% | 3.0% | 3.0% | 3.0% |
| methylparaben | 0.2% | 0.2% | 0.2% | 0.2% | 0.2% | 0.2% | 0.2% | 0.2% | 0.2% | 0.2% | 0.2% | 0.2% | 0.2% |
| propylparaben | 0.2% | 0.2% | 0.2% | 0.2% | 0.2% | 0.2% | 0.2% | 0.2% | 0.2% | 0.2% | 0.2% | 0.2% | 0.2% |
| AVB | 2.5% | 5.0% | 5.0% | — | — | — | 2.5% | 5.0% | 5.0% | 2.5% | 5.0% | 2.5% | 5.0% |
| OMC | — | — | — | 5.0% | 10.0% | 10.0% | 5.0% | 10.0% | 10.0% | — | — | 5.0% | 10.0% |
| EHPT | 5.0% | 5.0% | 10.0% | 5.0% | 5.0% | 10.0% | 5.0% | 5.0% | 10.0% | — | — | — | — |

TABLE 2

Photostability of the O/W formulations

| Formulation | Sun protection factor | | | UVA/UVB ratio | | | HPLC analysis | |
|---|---|---|---|---|---|---|---|---|
| | Initial value | % of initial value after 30 minutes | | Initial value | % of initial value after 30 minutes | | % degradation of AVB | % degradation of OMC |
| | | control | irradiated | | control | irradiated | | |
| 1 A | 17.3 ± 5.2 | 134 ± 14 | 127 ± 8 | 1.00 ± 0.01 | 100.7 ± 0.6 | 98.0 ± 1.0 | 36.9 ± 9.1 | — |
| 1 B | 17.5 ± 2.1 | 126 ± 12 | 155 ± 33 | 1.03 ± 0.02 | 100.6 ± 0.6 | 98.4 ± 0.6 | 13.7 ± 10.1 | — |
| 1 C | 24.0 ± 6.2 | 163 ± 25 | 133 ± 24 | 1.03 ± 0.02 | 100.6 ± 0.6 | 98.4 ± 0.6 | 8.5 ± 11.5 | — |
| 1 D | 23.5 ± 7.7 | 128 ± 18 | 105 ± 4 | 0.76 ± 0.02 | 97.8 ± 2.0 | 100.9 ± 0.8 | — | 29.8 ± 7.8 |
| 1 E | 39.4 ± 19.6 | 125 ± 19 | 140 ± 13 | 0.73 ± 0.03 | 95.9 ± 1.3 | 97.8 ± 0.7 | — | 27.4 ± 14.2 |
| 1 F | 37.7 ± 8.5 | 203 ± 32 | 204 ± 22 | 0.88 ± 0.02 | 96.2 ± 1.6 | 96.7 ± 1.0 | — | 22.0 ± 8.1 |
| 1 G | 22.8 ± 2.9 | 111 ± 9 | 93 ± 11 | 0.90 ± 0.01 | 99.3 ± 0.6 | 97.9 ± 1.1 | 13.1 | 39.3 ± 12.7 |
| 1 H | 82.2 ± 27.4 | 281 ± 22 | 194 ± 30 | 0.95 ± 0.01 | 96.2 ± 1.6 | 94.5 ± 0.6 | 36.9 ± 9.1 | 42.2 ± 7.3 |
| 1 I | 48.2 ± 27.4 | 187 ± 27 | 212 ± 43 | 0.97 ± 0.01 | 99.0 ± 0.1 | 98.0 ± 1.0 | 23.4 ± 13.8 | 30.9 ± 11.1 |
| 1 J | 3.3 ± 0.7 | 107 ± 2 | 56 ± 5 | 1.65 ± 0.13 | 99.4 ± 1.0 | 36.8 ± 6.2 | 69.0 ± 3.0 | — |
| 1 K | 2.8 ± 0.2 | 108 ± 2 | 77 ± 1 | 1.76 ± 0.07 | 96.4 ± 1.6 | 37.6 ± 4.0 | 64.4 ± 11.5 | — |
| 1 L | 17.6 ± 4.7 | 107 ± 5 | 32 ± 4 | 0.82 ± 0.02 | 99.6 ± 1.8 | 70.0 ± 11.6 | 66.4 ± 6.8 | 72.0 ± 6.3 |
| 1 M | 53.0 ± 13.3 | 143 ± 68 | 26 ± 6 | 0.87 ± 0.04 | 98.1 ± 1.7 | 74.3 ± 3.9 | 66.1 ± 1.1 | 70.7 ± 1.9 |

The results for formulations 1 J and 1 K confirm the inadequate photostability of AVB: most of the AVB was degraded under the test conditions, consequently resulting in pronounced decreases in the sun protection factor and the UVA/UVB ratio. In contrast, formulations 1 A to 1 C, which additionally comprise EHPT, showed no significant changes after irradiation with respect to the sun protection factor and the UVA/UVB ratio, which demonstrates the stabilising action of EHPT. Although the HPLC results do likewise show a certain amount of degradation of AVB, it was much less than in the case of AVB when used alone and clearly did not impair the protective action. In addition, the proportion of degraded AVB decreased as the concentration of AVB and/or EHPT increased.

The results for formulations 1 L and 1 M show that, although OMC is a potent UVB filter, it is likewise not stable in the presence of dibenzoylmethanes. In contrast, OMC is substantially stable in the presence of EHPT, as the results for formulations 1 D to 1 F show. However, the combination of AVB and OMC, especially, is clearly stabilised by the presence of EHPT, as can be seen from the results for formulations 1 G to 1 I. Although a certain, but clearly reduced amount of degradation of AVB and OMC was likewise found in the HPLC analysis, the effect on the sun protection factor and the UVA/UVB ratio was virtually negligible.

EXAMPLE 2

Phospholipid-Containing O/W Emulsions

In order to produce the phospholipid-containing O/W emulsions listed in Table 3, carbomer was in each case dispersed in water; sorbitol 70% and methylparaben were added to the dispersion, and the resulting aqueous phase was heated to 80° C. Triceteareth-4 phosphate, stearic acid, cetyl alcohol, dicaprylyl maleate, dimethicone, ($C_{12-15}$alkyl) benzoate, propylparaben, the UV filters AVB, OMC and/or EHPT and a solution of lecithin in ethanol 96% were mixed in a separate vessel, heated to 80° C. and then added to the heated aqueous phase. The mixture was homogenised for about 2 minutes, then cooled to ambient temperature, adjusted to a pH of 6.0–6.5 by adding tromethamine 20%, and again homogenised for about 2 minutes.

In accordance with the in vitro methods described above, the effect of UV light (30 minutes' irradiation with 30 MED) on the protective properties and the stability of the OIW emulsions was investigated. The measured sun protection factors and UVA/UVB ratios and their percentage changes (relative to the initial value), and the percentage degradation of AVB and/or OMC determined by means of HPLC, are indicated in Table 4. The values indicated are, in each case, averages (including scatter) from 3 measurements.

TABLE 3

Phospholipid-containing O/W formulations: compositions in % by weight

| Components | 2A | 2B | 2C | 2D | 2E | 2F | 2G | 2H | 2I | 2J | 2K | 2L | 2M |
|---|---|---|---|---|---|---|---|---|---|---|---|---|---|
| water | 71.1% | 68.6% | 63.6% | 68.6% | 63.6% | 58.6% | 66.1% | 58.6% | 53.5% | 76.1% | 73.6% | 71.1% | 63.6% |
| carbomer | 0.2% | 0.2% | 0.2% | 0.2% | 0.2% | 0.2% | 0.2% | 0.2% | 0.2% | 0.2% | 0.2% | 0.2% | 0.2% |
| tromethamine 20% | 0.8% | 0.8% | 0.8% | 0.8% | 0.8% | 0.8% | 0.8% | 0.8% | 0.9% | 0.8% | 0.8% | 0.8% | 0.8% |
| sorbitol 70% | 3.0% | 3.0% | 3.0% | 3.0% | 3.0% | 3.0% | 3.0% | 3.0% | 3.0% | 3.0% | 3.0% | 3.0% | 3.0% |
| ethanol 96% | 2.5% | 2.5% | 2.5% | 2.5% | 2.5% | 2.5% | 2.5% | 2.5% | 2.5% | 2.5% | 2.5% | 2.5% | 2.5% |
| triceteareth-4 phosphate | 4.0% | 4.0% | 4.0% | 4.0% | 4.0% | 4.0% | 4.0% | 4.0% | 4.0% | 4.0% | 4.0% | 4.0% | 4.0% |
| stearic acid | 3.0% | 3.0% | 3.0% | 3.0% | 3.0% | 3.0% | 3.0% | 3.0% | 3.0% | 3.0% | 3.0% | 3.0% | 3.0% |
| cetyl alcohol | 0.5% | 0.5% | 0.5% | 0.5% | 0.5% | 0.5% | 0.5% | 0.5% | 0.5% | 0.5% | 0.5% | 0.5% | 0.5% |
| dicaprylyl maleate | 3.0% | 3.0% | 3.0% | 3.0% | 3.0% | 3.0% | 3.0% | 3.0% | 3.0% | 3.0% | 3.0% | 3.0% | 3.0% |
| lecithin | 0.5% | 0.5% | 0.5% | 0.5% | 0.5% | 0.5% | 0.5% | 0.5% | 0.5% | 0.5% | 0.5% | 0.5% | 0.5% |

TABLE 3-continued

Phospholipid-containing O/W formulations: compositions in % by weight

| Components | 2A | 2B | 2C | 2D | 2E | 2F | 2G | 2H | 2I | 2J | 2K | 2L | 2M |
|---|---|---|---|---|---|---|---|---|---|---|---|---|---|
| dimethicone | 0.5% | 0.5% | 0.5% | 0.5% | 0.5% | 0.5% | 0.5% | 0.5% | 0.5% | 0.5% | 0.5% | 0.5% | 0.5% |
| ($C_{12}$–$C_{15}$alkyl) benzoate | 3.0% | 3.0% | 3.0% | 3.0% | 3.0% | 3.0% | 3.0% | 3.0% | 3.0% | 3.0% | 3.0% | 3.0% | 3.0% |
| methylparaben | 0.2% | 0.2% | 0.2% | 0.2% | 0.2% | 0.2% | 0.2% | 0.2% | 0.2% | 0.2% | 0.2% | 0.2% | 0.2% |
| propylparaben | 0.2% | 0.2% | 0.2% | 0.2% | 0.2% | 0.2% | 0.2% | 0.2% | 0.2% | 0.2% | 0.2% | 0.2% | 0.2% |
| AVB | 2.5% | 5.0% | 5.0% | — | — | — | 2.5% | 5.0% | 5.0% | 2.5% | 5.0% | 2.5% | 5.0% |
| OMC | — | — | — | 5.0% | 10.0% | 10.0% | 5.0% | 10.0% | 10.0% | — | — | 5.0% | 10.0% |
| EHPT | 5.0% | 5.0% | 10.0% | 5.0% | 5.0% | 10.0% | 5.0% | 5.0% | 10.0% | — | — | — | — |

TABLE 4

Photostability of the phospholipid-containing O/W formulations

| Formu-lation | Sun protection factor | | | UVA/UVB ratio | | | HPLC analysis | |
|---|---|---|---|---|---|---|---|---|
| | Initial value | % of initial value after 30 minutes | | Initial value | % of initial value after 30 minutes | | % degrada-tion of AVB | % degrada-tion of OMC |
| | | control | irradiated | | control | irradiated | | |
| 2 A | 23.2 ± 8.9 | 113 ± 4 | 107 ± 8 | 1.01 ± 0.01 | 101.0 ± 1.0 | 97.0 ± 1.6 | 4.2 ± 12.9 | — |
| 2 B | 27.7 ± 8.3 | 111 ± 8 | 112 ± 12 | 1.04 ± 0.02 | 100.3 ± 0.6 | 95.9 ± 2.3 | 1.61 | — |
| 2 C | 17.6 ± 2.5 | 108 ± 5 | 102 ± 4 | 1.02 ± 0.01 | 100.0 ± 0.0 | 99.3 ± 0.6 | 0.6 ± 11.0 | — |
| 2 D | 20.4 ± 5.4 | 113 ± 8 | 103 ± 3 | 0.77 ± 0.05 | 98.7 ± 1.2 | 103.1 ± 0.8 | — | 17.4 ± 32.6 |
| 2 E | 43.2 ± 28.9 | 127 ± 1 | 107 ± 7 | 0.74 ± 0.02 | 97.7 ± 0.8 | 101.8 ± 0.9 | — | 27.1 ± 0.6 |
| 2 F | 22.8 ± 4.3 | 122 ± 11 | 106 ± 4 | 0.89 ± 0.02 | 98.5 ± 1.3 | 101.8 ± 3.2 | — | * |
| 2 G | 16.5 ± 0.9 | 119 ± 8 | 105 ± 11 | 0.94 ± 0.01 | 99.3 ± 0.6 | 97.5 ± 0.6 | 26.9 ± 10.7 | 23.0 ± 34.8 |
| 2 H | 25.5 ± 6.0 | 143 ± 22 | 129 ± 24 | 0.98 ± 0.02 | 98.6 ± 1.2 | 96.9 ± 0.1 | 17.8 ± 0.7 | 25.2 ± 0.6 |
| 2 I | 25.1 ± 6.9 | 124 ± 15 | 109 ± 8 | 0.99 ± 0.02 | 98.3 ± 1.6 | 99.3 ± 1.6 | 16.7 ± 7.8 | 28.4 ± 4.1 |
| 2 J | 3.7 ± 0.6 | 101 ± 1 | 49 ± 11 | 1.79 ± 0.12 | 100.4 ± 1.4 | 37.8 ± 8.0 | 57.4 ± 11.9 | — |
| 2 K | 3.0 ± 0.3 | 115 ± 2 | 63 ± 9 | 1.73 ± 0.11 | 97.1 ± 0.9 | 23.4 ± 5.4 | 56.3 ± 8.4 | — |
| 2 L | 13.0 ± 2.4 | 103 ± 5 | 18 ± 3 | 0.81 ± 0.01 | 100.0 ± 0.0 | 52.8 ± 5.2 | 58.0 ± 5.9 | 64.0 ± 4.1 |
| 2 M | 45.5 ± 18.7 | 110 ± 9 | 21 ± 9 | 0.88 ± 0.03 | 98.9 ± 1.1 | 65.3 ± 5.8 | 48.7 ± 4.2 | 54.8 ± 3.4 |

*not determined

The results for formulations 2 J and 2 K confirm the inadequate photostability of AVB: most of the AVB was degraded under the test conditions, consequently resulting in pronounced decreases in the sun protection factor and the UVA/UVB ratio. In contrast, formulations 2 A to 2 C, which additionally comprise EHPT, showed no significant changes after irradiation with respect to the sun protection factor and the UVA/UVB ratio, which demonstrates the stabilising action of EHPT. The HPLC results show that only very little degradation of AVB took place and that this was also lower than in the case of the O/W emulsions not containing phospholipid (cf. formulations 1 A to 1C of Example 1).

The results for formulations 2 L and 2 M confirm that, although OMC is a potent UVB filter, it is likewise not stable in the presence of dibenzoylmethanes. In contrast, OMC is substantially stable in the presence of EHPT, as the results for formulations 2 D to 2 F show. However, the combination of AVB and OMC, especially, is clearly stabilised by the presence of EHPT, as can be seen from the results for formulations 2 G to 2 I. Although a certain, but clearly reduced amount of degradation of AVB and OMC was likewise found in the HPLC analysis, the effect on the sun protection factor and the UVA/UVB ratio was virtually negligible. In addition, the proportion of degraded AVB and OMC again tended to be lower than in the case of the corresponding O/W emulsions not containing phospholipid (cf. formulations 1 G to 1 I of Example 1).

EXAMPLE 3

W/O Emulsions

In order to produce the W/O emulsions listed in Table 5, in each case water, sodium lactate solution and lactic acid were mixed, methylparaben was added and the resulting aqueous phase was heated to 80° C. PEG-7-hydrogenated castor oil, methoxy-PEG-22/dodecyl glycol copolymer, Arlacel 582, myristyl lactate, medium-chain-length triglyceride, paraffin, dimethicone, propylparaben and the UV filters AVB, OMC and/or EHPT were mixed in a separate vessel, heated to 80° C. and then added to the aqueous phase. The mixture was homogenised for about 2 minutes, then cooled to ambient temperature; benzyl alcohol was added and homogenisation was again carried out for about 2 minutes.

In accordance with the in vitro methods described above, the effect of UV light (30 minutes' irradiation with 30 MED) on the protective properties and the stability of the O/W emulsions was investigated. The measured sun protection factors and UVA/UVB ratios and their percentage changes (relative to the initial value), and the percentage degradation of AVB and/or OMC determined by means of HPLC, are indicated in Table 6. The values indicated are, in each case, averages (including scatter) from 3 measurements.

TABLE 5

W/O formulations: compositions in % by weight

| Components | 3A | 3B | 3C | 3D | 3E | 3F | 3G | 3H | 3I | 3J |
|---|---|---|---|---|---|---|---|---|---|---|
| water | 56.2% | 53.7% | 48.7% | 51.2% | 43.7% | 38.7% | 61.2% | 58.7% | 56.2% | 48.7% |
| sodium lactate solution | 2.2% | 2.2% | 2.2% | 2.2% | 2.2% | 2.2% | 2.2% | 2.2% | 2.2% | 2.2% |
| lactic acid | 0.2% | 0.2% | 0.2% | 0.2% | 0.2% | 0.2% | 0.2% | 0.2% | 0.2% | 0.2% |
| PEG-7-hydr. castor oil | 3.0% | 3.0% | 3.0% | 3.0% | 3.0% | 3.0% | 3.0% | 3.0% | 3.0% | 3.0% |
| methoxy-PEG-22/dodecyl glycol copolymer | 2.0% | 2.0% | 2.0% | 2.0% | 2.0% | 2.0% | 2.0% | 2.0% | 2.0% | 2.0% |
| Arlacel 582 | 3.0% | 3.0% | 3.0% | 3.0% | 3.0% | 3.0% | 3.0% | 3.0% | 3.0% | 3.0% |
| myristyl lactate | 2.5% | 2.5% | 2.5% | 2.5% | 2.5% | 2.5% | 2.5% | 2.5% | 2.5% | 2.5% |
| medium-chain-length triglyceride | 5.0% | 5.0% | 5.0% | 5.0% | 5.0% | 5.0% | 5.0% | 5.0% | 5.0% | 5.0% |
| paraffin | 15.0% | 15.0% | 15.0% | 15.0% | 15.0% | 15.0% | 15.0% | 15.0% | 15.0% | 15.0% |
| dimethicone | 2.0% | 2.0% | 2.0% | 2.0% | 2.0% | 2.0% | 2.0% | 2.0% | 2.0% | 2.0% |
| benzyl alcohol | 1.0% | 1.0% | 1.0% | 1.0% | 1.0% | 1.0% | 1.0% | 1.0% | 1.0% | 1.0% |
| methylparaben | 0.2% | 0.2% | 0.2% | 0.2% | 0.2% | 0.2% | 0.2% | 0.2% | 0.2% | 0.2% |
| propylparaben | 0.2% | 0.2% | 0.2% | 0.2% | 0.2% | 0.2% | 0.2% | 0.2% | 0.2% | 0.2% |
| AVB | 2.5% | 5.0% | 5.0% | 2.5% | 5.0% | 5.0% | 2.5% | 5.0% | 2.5% | 5.0% |
| OMC | — | — | 5.0% | 10.0% | 10.0% | — | — | 5.0% | 10.0% | — |
| EHPT | 5.0% | 5.0% | 10.0% | 5.0% | 5.0% | 10.0% | — | — | — | — |

TABLE 6

Photostability of the W/O formulations

| Formulation | Sun protection factor | | | UVA/UVB ratio | | | HPLC analysis | |
|---|---|---|---|---|---|---|---|---|
| | Initial value | % of initial value after 30 minutes | | Initial value | % of initial value after 30 minutes | | % degradation of AVB | % degradation of OMC |
| | | control | irradiated | | control | irradiated | | |
| 3 A | 34.8 ± 13.2 | 141 ± 10 | 142 ± 23 | 1.01 ± 0.02 | 100.0 ± 0.0 | 97.3 ± 0.6 | 17.5 ± 5.8 | — |
| 3 B | 34.1 ± 8.9 | 155 ± 22 | 151 ± 31 | 1.01 ± 0.02 | 100.7 ± 0.6 | 99.7 ± 0.6 | 14.7 ± 12.0 | — |
| 3 C | 62.4 ± 33.7 | 146 ± 11 | 151 ± 12 | 0.99 ± 0.01 | 99.7 ± 0.6 | 99.0 ± 0.1 | 10.8 ± 22.7 | — |
| 3 D | 76.0 ± 34.6 | 130 ± 61 | 154 ± 12 | 0.93 ± 0.01 | 97.1 ± 0.6 | 96.1 ± 0.6 | 19.2 ± 11.8 | 29.9 ± 10.8 |
| 3 E | 45.2 ± 20.9 | 209 ± 114 | 257 ± 108 | 0.97 ± 0.01 | 96.9 ± 1.0 | 94.8 ± 1.1 | 20.3 ± 7.6 | 30.6 ± 5.8 |
| 3 F | 117.4 ± 21.2 | 190 ± 21 | 163 ± 60 | 0.96 ± 0.03 | 97.6 ± 0.6 | 95.7 ± 1.2 | 7.6 ± 2.0 | 16.9 ± 2.1 |
| 3 G | 5.4 ± 1.1 | 105 ± 3 | 29 ± 3 | 1.60 ± 0.19 | 104.6 ± 3.0 | 52.2 ± 7.8 | 65.0 ± 18.9 | — |
| 3 H | 4.7 ± 0.7 | 106 ± 6 | 41 ± 1 | 1.71 ± 0.11 | 100.7 ± 2.5 | 44.2 ± 0.7 | 69.3 ± 8.1 | — |
| 3 I | 40.0 ± 10.0 | 136 ± 48 | 35 ± 6 | 0.85 ± 0.02 | 96.9 ± 0.6 | 68.3 ± 3.2 | 64.6 ± 2.7 | 67.4 ± 1.9 |
| 3 J | 63.8 ± 40.8 | 244 ± 54 | 69 ± 25 | 0.95 ± 0.02 | 93.7 ± 0.9 | 77.3 ± 5.7 | 58.6 ± 5.7 | 65.1 ± 5.5 |

The results for formulations 3 G and 3 H confirm the inadequate photostability of AVB: most of the AVB was degraded under the test conditions, consequently resulting in pronounced decreases in the sun protection factor and the UVA/UVB ratio. In contrast, formulations 3 A to 3 C, which additionally comprise EHPT, showed no significant changes after irradiation with respect to the sun protection factor and the UVA/UVB ratio, which demonstrates the stabilising action of EHPT. Although the HPLC results do show a certain amount of degradation of AVB, it was much less than in the case of AVB when used alone and clearly did not impair the protective action. In addition, the proportion of degraded AVB appears to decrease along with an increase in the concentration of AVB and/or EHPT.

The results for formulations 3 I and 3 J confirm that, although OMC is a potent UVB filter, it is likewise not stable in the presence of dibenzoylmethanes. However, the combination of AVB and OMC is clearly stabilised by the presence of EHPT, as can be seen from the results for formulations 3 D to 3 F. Although a certain, but clearly reduced amount of degradation of AVB and OMC was likewise found in the HPLC analysis, the effect on the sun protection factor and the UVA/UVB ratio was virtually negligible. In addition, a tendency for the proportion of degraded AVB and OMC to be lower in the case of increased EHPT concentration was again demonstrated.

What is claimed is:

1. A method of improving the photostability of a dibenzaylmethane derivative, which comprises adding an effective photostabilizing amount of 2,4-bis[[4-(2-ethylhexyloxy)-2-hydroxy]-phenyl]-6-(4-methoxyphenyl)-1,3,5-triazine thereto.

2. A method for the production of a cosmetic composition comprising a dibenzoylmethane derivative, which comprises adding an amount of 2,4-bis[[4-(2-ethylhexyloxy)-2-hydroxy]phenyl]-6-(4-methoxyphenyl)-1,3,5-triazine which is effective for the purpose of improving the photostability of the dibenzoylmethane derivative thereto.

3. A method according to claim 1, wherein the dibenzoylmethane derivative is 4-tert-butyl-4'-methoxydibenzoylmethane.

4. A method according to claim 2, wherein the dibenzoylmethane derivative is 4-tert-butyl-4'-methoxydibenzoylmethane.

5. A method according to claim 2, wherein the cosmetic composition has a ratio of UVA absorbance to UVB absorbance of from 0.6 to 1.5.

6. A method according 5, wherein the cosmetic composition has a ratio of UVA absorbance to UVB absorbance of from 0.8 to 1.1.

7. A method according to claim 2, wherein 2,4-bis[[4-(2-ethylhexyloxy)-2-hydroxy]phenyl]-6-(4-methoxyphenyl)-1,3,5-triazine is used in an amount of from 0.1 to 15% by weight based on the cosmetic formulation.

8. A method according to claim 7, wherein 2,4-bis[[4-(2-ethylhexyloxy)-2-hydroxy]phenyl]6-(4-methoxyphenyl)-1,3,5-triazine is used in an amount of from 0.5 to 10% by weight based on the cosmetic formulation.

9. A method according to claim 2, wherein the cosmetic composition contains from 0.1 to 10% by weight of dibenzoylmethane derivative.

10. A method according to claim 9, wherein the cosmetic composition contains from 0.5 to 5% by weight of the dibenzoylmethane derivative.

11. A method according to claim 2, wherein the cosmetic composition additionally comprises a cinnamic acid ester.

12. A method according to claim 11, wherein the cinnamic acid ester is 4-methoxycinnamic acid 2-ethylhexyl ester or 4-methoxycinnamic acid isoamyl ester.

13. A method according to claim 11, wherein the cosmetic composition contains from 0.1 to 15% by weight of the cinnamic acid ester.

14. A method according to claim 2, wherein the cosmetic composition is an emulsion.

15. A method according to claim 14, wherein the cosmetic composition is an oil-in-water emulsion or a water-in-oil emulsion.

16. A method according to claim 14, wherein the emulsion comprises a phospholipid.

17. A method according to claim 16, wherein the emulsion comprises lecithin.

18. A topical cosmetic composition for protection against UV radiation, which comprises a cosmetically acceptable carrier, at least one dibenzoylmethane derivative, at least one cinnamic acid ester and an effective amount of 2,4-bis[[4-(2-ethylhexyloxy)-2-hydroxy]phenyl]-6-(4-methoxyphenyl)-1,3,5-triazine.

19. A method to the production of a topical cosmetic composition for use for protection against UV radiation which comprises a cosmetically acceptable carrier, at least one dibenzoylmethane derivative, at least one cinnamic acid ester and an effective amount of 2,4-bis[[4-(2-ethylhexyloxy)-2-hydroxy]phenyl]-6-(4-methoxyphenyl)-1,3,5-triazine, which method comprises incorporating the dibenzoylmethane deriative, the cinnamic acid ester and 2,4-bis[[4-(2-ethylhexyloxy)-2-hydroxy]phenyl]-6-(4-methoxyphenyl)-1,3,5-triazine into the cosmetically acceptable carrier.

* * * * *